US011898058B2

(12) United States Patent
Friedrich

(10) Patent No.: US 11,898,058 B2
(45) Date of Patent: *Feb. 13, 2024

(54) FLUORINE COMPOUNDS

(71) Applicant: Merck Patent GmbH, Darmstadt (DE)

(72) Inventor: Reiner Friedrich, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 124 days.

This patent is subject to a terminal disclaimer.

(21) Appl. No.: 17/377,912

(22) Filed: Jul. 16, 2021

(65) Prior Publication Data

US 2021/0340383 A1 Nov. 4, 2021

Related U.S. Application Data

(62) Division of application No. 15/536,671, filed as application No. PCT/EP2015/002530 on Dec. 16, 2015, now Pat. No. 11,118,066.

(30) Foreign Application Priority Data

Dec. 19, 2014 (EP) .................................... 14004337

(51) Int. Cl.
| | | |
|---|---|---|
| C09D 5/00 | (2006.01) | |
| C07F 7/18 | (2006.01) | |
| C07C 323/12 | (2006.01) | |
| C09D 4/00 | (2006.01) | |
| C07C 69/653 | (2006.01) | |
| C07C 319/12 | (2006.01) | |

(52) U.S. Cl.
CPC .............. C09D 5/00 (2013.01); C07C 69/653 (2013.01); C07C 319/12 (2013.01); C07C 323/12 (2013.01); C07F 7/1804 (2013.01); C09D 4/00 (2013.01)

(58) Field of Classification Search
None
See application file for complete search history.

(56) References Cited

U.S. PATENT DOCUMENTS

| | | | |
|---|---|---|---|
| 6,255,535 | B1 | 1/2001 | Schulz et al. |
| 6,809,216 | B2 | 10/2004 | Bradley et al. |
| 7,737,307 | B2 | 6/2010 | Murphy |
| 8,173,848 | B2 | 5/2012 | Mclain |
| 8,263,800 | B2 | 9/2012 | Murphy |
| 8,614,347 | B2 | 12/2013 | Percec |
| 8,697,831 | B2 | 4/2014 | Drysdale |
| 9,416,085 | B2 | 8/2016 | Marchionni |
| 2003/0109626 | A1 | 6/2003 | Bradley et al. |
| 2005/0107645 | A1 | 5/2005 | Furukawa |
| 2005/0113609 | A1 | 5/2005 | Furukawa |
| 2006/0222865 | A1 | 10/2006 | Hoshino et al. |
| 2009/0023948 | A1 | 1/2009 | Yamaguchi et al. |
| 2009/0176942 | A1 | 7/2009 | Ishikawa et al. |
| 2010/0004478 | A1 | 1/2010 | Mclain |
| 2012/0277460 | A1 | 11/2012 | Percec |
| 2012/0329976 | A1 | 12/2012 | Drysdale |
| 2016/0229875 | A1 | 8/2016 | Qiu |
| 2017/0121260 | A1 | 5/2017 | Friedrich |

FOREIGN PATENT DOCUMENTS

| | | | |
|---|---|---|---|
| CN | 1665768 | A | 9/2005 |
| CN | 1665769 | A | 9/2005 |
| CN | 102083779 | A | 6/2011 |
| EP | 0075865 | A2 | 4/1983 |
| EP | 1522536 | A1 | 4/2005 |
| JP | 50052019 | A | 5/1975 |
| JP | H01226844 | A | 9/1989 |
| JP | 2003518052 | A | 6/2003 |
| JP | 2004043402 | A2 | 2/2004 |
| JP | 2004212620 | A | 7/2004 |
| JP | 2004531617 | A | 10/2004 |
| JP | 2007238583 | A | 9/2007 |
| JP | 2012087092 | A2 | 5/2012 |
| JP | 2014162742 | A2 | 9/2014 |
| KR | 20060108616 | A | 10/2006 |
| WO | 02102758 | A1 | 12/2002 |
| WO | 2009020907 | A1 | 2/2009 |
| WO | 10003931 | A1 | 1/2010 |
| WO | 2010002623 | A2 | 1/2010 |
| WO | 2010003931 | A1 | 1/2010 |
| WO | 2015050740 | A1 | 4/2015 |
| WO | 2015124290 | A1 | 8/2015 |

OTHER PUBLICATIONS

Notice of Grounds for Rejection in corresponding Korean Patent Application No. 10-2017-7019860 dated Oct. 17, 2022 ( pp. 1-20 ) and english translation thereof (pp. 1-20).
English translation of JP2007238583A issued Sep. 29, 2007 to Matsukawa Yasuhisa of Nat Inst of Adv Ind & Technol entitled Fluorine-Containing Polyether Compound and Its Production Method.
Database Ca [online] Chemical Abstracts Service, Columbus, Ohio, US; 1953, Knunyants, I.L. et al.: "Addition reactions of fluoroolefins II. Addition of alcohols and thiols to perfluoropropylene", XP002754717, Database accession No. 48:32423.
Cirkva V et al: "Radical additions to fluoroolefins. Photochemical fluoroalkylation of alkanols and alkane diols with perfluoro vinyl ethers; photo-supported O-alkylation of butane-1,4-diol with hexafluoropropene", Journal of Fluorine Chemistry, Elsevier, NL, vol. 80, No. 2, Oct. 1, 1996 (Oct. 1, 1996), pp. 135-144, XP004071321, ISSN: 0022-1139, DOI: 10.1016/S0022-1139(96)03514-2.
A. A. Il'inA. et. al., "Promising prospects for using partially fluorinated alcohols as O-nucleophilic reagents in organofluoric synthesis" Russian J. Applied Chem 2007, vol. 80, No. 3, 405-418.
Knunyants, I.L. et al.: "Addition reactions of fluoroolefins II. Addition of alcohols and thiols to perfluoropropylene", Izvestiya Akademii Nauk SSSR, Seriya Khimicheskaya, 1953, pp. 282-289, ISSN: 0002-3353 (See CAS abstract).
Communication dated Feb. 24, 2021 in corresponding EP 15817072 (pp. 1-4).

(Continued)

*Primary Examiner* — Yun Qian

(74) *Attorney, Agent, or Firm* — Millen, White, Zelano & Branigan, P.C.; Brion P. Heaney

(57) ABSTRACT

The present invention relates to novel compounds containing fluorinated end groups and to the use thereof in, for example, dirt-repellent coatings.

14 Claims, No Drawings

(56) References Cited

OTHER PUBLICATIONS

Communication dated Nov. 12, 2020 in corresponding EP 15817072 {pp. 1-6}.
Knunyants et al.: Addition reactions of fluoroalkenes, Bulletin of the Akademy of Science of the USSR 1953, 2, 55-261.
Office Action in corresponding CN application dated Feb. 3, 2020 pp. 1-23.
Boutevin et al., J. Fluorine Chem., 1989, 45, 355-376.
Office Action issued in corresponding Examination Procedure in Japanese Patent Application No. 2017-533230 {dated Sep. 18, 2019) pp. 1-2.
Serdyuk et al., "Polyfluoroalkylthiotrifluoroacetylketenes", Russian Chemical Bulletin International Edition 2003, 52, 8, 1854-1858, XP055818966.
Haszeldine et al., Fluoro-olefin chemistry. Part 11. Some reactions of perfluoro-3-methylbut-1-ene under ionic and freeradical conditions,Journal of the Chemical Society, Perkin Transactions 1979, 565, XP055818969.
Harris et al., "The Free Radical Addition of Trifluoromethanethiol to Fluoroolefins", Journal of the American Chemical Society 1961, 83, 4, 840-845, XP055818971.
Koob at al., "Metabolism of hexafluoropropene. Evidence for bioactivation by glutathione conjugate formation in the kidney",Drug Metabolism and Disposition, Pharmacology and Experimental Therapeutics 1990, 18, 6, 911-916, XP009528357.

FLUORINE COMPOUNDS

The present invention relates to novel compounds containing fluorinated end groups and to the use thereof in, for example, dirt-repellent coatings Dirt-repellent coatings, for example in the display industry, consist principally of perfluorinated compounds which can be bonded to surfaces by means of siloxane groups. Dirt-repellent coatings in the textile industry consist principally of perfluorinated compounds which can be bonded to surfaces by means of acrylate, methacrylate or siloxane groups. Owing to their chemical stability, these compounds have been criticised over the years since the perfluorinated content of this class of materials cannot be degraded by natural means. In addition, it has not unambiguously been clarified what influence these long-lived materials have on the biosphere and whether they result in bioaccumulation in various animal species.

There is therefore a demand for alternative substances for dirt-repellent coatings.

The present invention relates firstly to compounds of the formulae (I) or (I')

$$(Rf-CHF-CF_2-O-CHR)_m-L-(X)_n \quad (I)$$

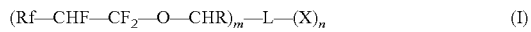

$$(Rf-CHF-CF_2-S-CHR)_m-L-(X)_n \quad (I')$$

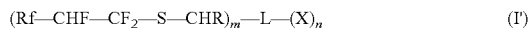

where
Rf=a perfluorinated alkyl group, optionally containing heteroatoms,
R=H or an alkyl group,
L=a single bond or a divalent organic group,
X=an anchor group,
m is $\geq 1$
and n is $\geq 1$.

The perfluorinated group Rf is preferably selected from the groups:
$CF_3-(CF_2)_{0-3}-$, $CF_3-(CF_2)_{0-3}-O-$, $CF_3-(CF_2)_{0-3}-O-(CF_2)_{1-3}-$,
$CF_3-(CF_2)_{0-3}-O-(CF_2)_{1-3}-O-$, $CF_3-(CF_2)_{0-3}-O-(CF_2)_{1-3}-O-CF_2-$, $CF_3-(CF_2)_{0-3}O-(CF_2-O)_{1-8}-$ and $CF_3-(CF_2)_{0-3}-O-(CF_2-O)_{1-8}-CF_2-$.

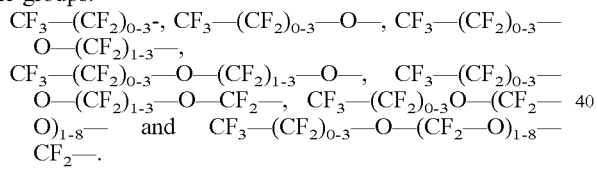

The perfluorinated group Rf is particularly preferably selected from the groups:
$CF_3-(CF_2)_{1-2}-$, $CF_3-(CF_2)_{1-2}-O-$, $CF_3-O-(CF_2)_{1-3}-$, $CF_3-O-(CF_2)_{1-3}-O-$, $CF_3-(CF_2)_{1-2}-O-CF2-$, $CF_3-O-(CF_2)_{1-2}-O-CF_2-$, $CF_3-O-(CF_2-O)_{1-8}-$ and $CF_3-O-(CF_2-O)_{1-8}-CF_2-$.

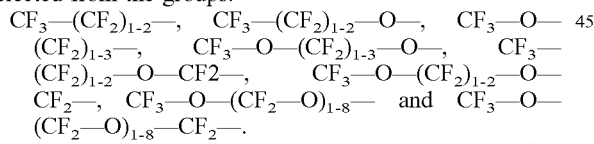

In a variant, the perfluorinated group Rf can also preferably be selected from the groups $CF_3-(CF_2)_{0-3}-$, $CF_3-(CF_2)_{0-3}-O-$, $CF_3-O-(CF_2)_{1-3}-$ and $CF_3-O-(CF_2)_{1-3}-O-$, in particular from the groups $CF_3-(CF_2)_{1-2}-$, $CF_3-(CF_2)_{1-2}-O-$, $CF_3-O-(CF_2)_{1-2}-$ and $CF_3-O-(CF_2)_{1-3}-O-$.

The group R is preferably equal to H or C1-C3 alkyl, in particular H or a methyl group.

L is preferably a single bond or a saturated or unsaturated, branched or unbranched hydrocarbon unit, optionally containing heteroatoms and/or functional groups. L is particularly preferably a single bond or a saturated, branched or unbranched alkylene group, optionally containing heteroatoms and/or functional groups.

The group X is an anchor group which is suitable for facilitating adhesion of the compounds of the formula (I) to substrate surfaces, such as, for example, textiles or glass surfaces. In other words, the group X is preferably a reactive group which forms a covalent bond to substrate surfaces. X is preferably an ethylenically unsaturated group, in particular an acrylate or methacrylate group, an alkoxysilane group or a halosilane group. X may be an $-SiR'_3$, where the groups R' are, independently of one another, equal to alkyl, OH, halogen, alkoxy or aryloxy, where at least one group R' is not an alkyl group. R' is preferably an alkoxy group OR", where R" is equal to C1-C4-alkyl, in particular C1- or C2-alkyl.

In particular for bonding to glass surfaces, X is preferably an alkoxysilane group $-Si(OR"_3)_3$, where R" is equal to C1-C4-alkyl, in particular C1- or C2-alkyl.

In a particularly preferred variant of the invention, in particular for bonding to textile surfaces, X is preferably an acrylate or methacrylate group.

m is preferably 1-3, in particular 1 or 2.
n is preferably 1-3, in particular 1.

Particularly advantageous are compounds of the formulae (I) and (I') in which one or more of the variables have the preferred meanings. Compounds in which all variables have the preferred meanings are especially advantageous. Particular preference is given to compounds where:
Rf=$CF_3-(CF_2)_{1-2}-$, $CF_3-(CF_2)_{1-2}-O-$, $CF_3-O-(CF_2)_{1-3}-$, $CF_3-O-(CF_2)_{1-3}-O-$, $CF_3-(CF_2)_{1-2}-O-CF2-$, $CF_3-O-(CF_2)_{1-2}-O-CF_2-$, $CF_3-O-(CF_2-O)_{1-8}-$ and $CF_3-O-(CF_2-O)_{1-8}-CF_2-$, R=H or $CH_3$,

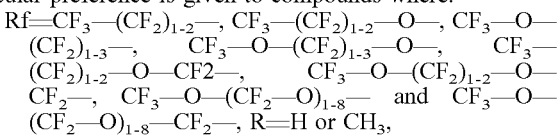

L=a single bond or a C1-C4-alkylene group, which is optionally branched and/or contains a functional group,
X=an alkoxysilane group $-Si(OR"_3)_3$, where R" is equal to C1- or C2-alkyl, and m=1 or 2 and n=1.

Particular preference is also given to compounds where:
Rf=$CF_3-(CF_2)_{1-2}-$, $CF_3-(CF_2)_{1-2}-O-$, $CF_3-O-(CF_2)_{1-3}-$, $CF_3-O-(CF_2)_{1-3}-O-$, $CF_3-(CF_2)_{1-2}-O-CF2-$, $CF_3-O-(CF_2)_{1-2}-O-CF_2-$, $CF_3-O-(CF_2-O)_{1-8}-$ and $CF_3-O-(CF_2-O)_{1-8}-CF_2-$,
R=H or $CH_3$,

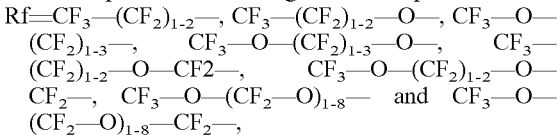

L=a single bond or a C1-C4-alkylene group, which is optionally branched and/or contains heteroatoms, in particular O, and/or a functional group, in particular OH,
X=an acrylate or methacrylate group, and
m=1 or 2 and n=1.

Particular preference is given to compounds of the formulae (Ia) to (Ih) and/or (I'a) to (I'h), where Rf=a perfluorinated alkyl group, optionally containing heteroatoms, R"=C1-C4-alkyl, in particular C1- or C2-alkyl, R'"=H or an alkyl group, preferably is equal to H or methyl, and $R^1$ is equal to H or C1-C4-alkyl, preferably H or $CH_3$.

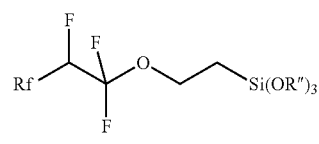

(Ia)

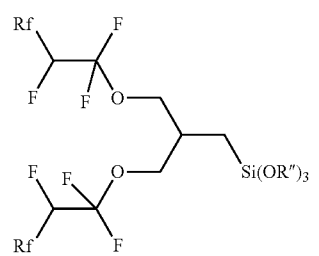

(Ib)

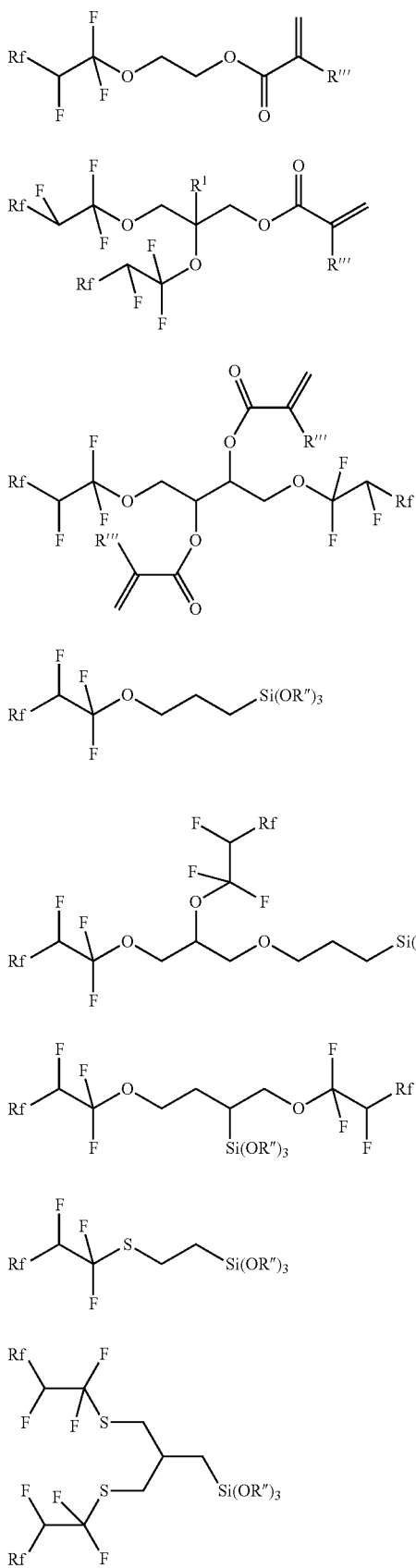
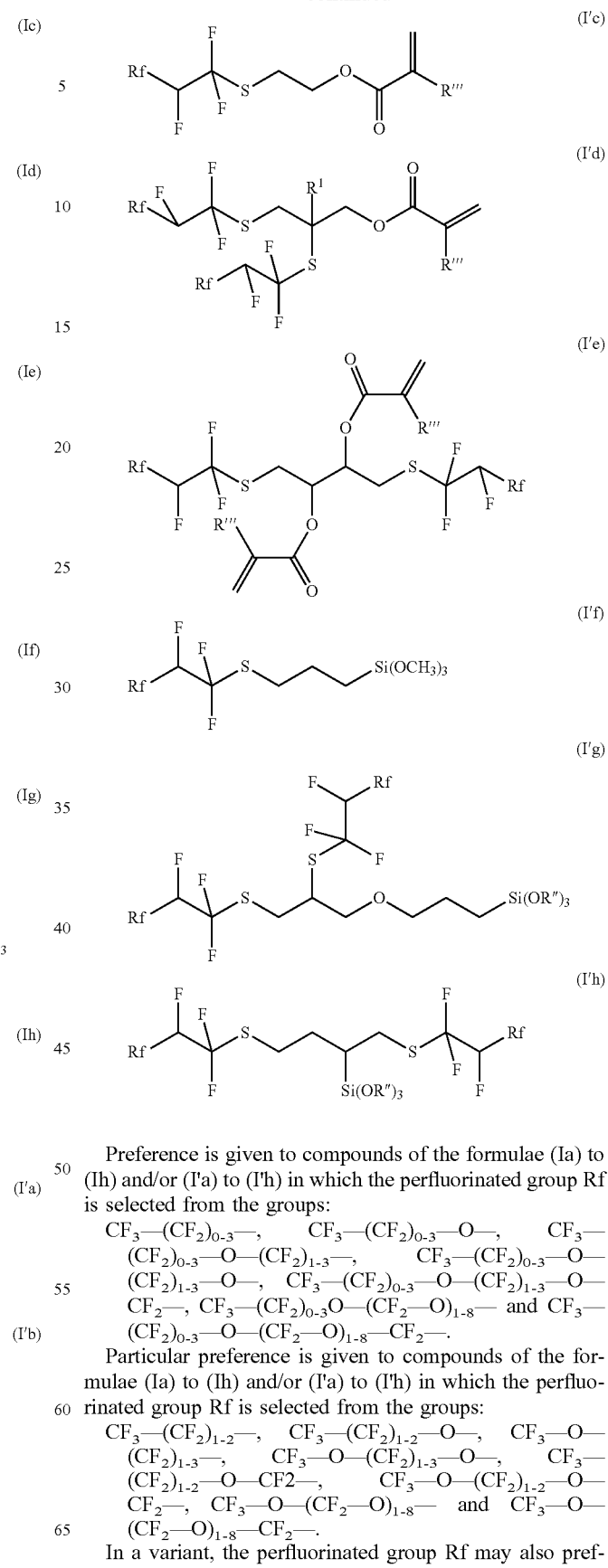

Preference is given to compounds of the formulae (Ia) to (Ih) and/or (I'a) to (I'h) in which the perfluorinated group Rf is selected from the groups:

$CF_3-(CF_2)_{0-3}-$, $CF_3-(CF_2)_{0-3}-O-$, $CF_3-(CF_2)_{0-3}-O-(CF_2)_{1-3}-$, $CF_3-(CF_2)_{0-3}-O-(CF_2)_{1-3}-O-$, $CF_3-(CF_2)_{0-3}-O-(CF_2)_{1-3}-O-CF_2-$, $CF_3-(CF_2)_{0-3}O-(CF_2-O)_{1-8}-$ and $CF_3-(CF_2)_{0-3}-O-(CF_2-O)_{1-8}-CF_2-$.

Particular preference is given to compounds of the formulae (Ia) to (Ih) and/or (I'a) to (I'h) in which the perfluorinated group Rf is selected from the groups:

$CF_3-(CF_2)_{1-2}-$, $CF_3-(CF_2)_{1-2}-O-$, $CF_3-O-(CF_2)_{1-3}-$, $CF_3-O-(CF_2)_{1-3}-O-$, $CF_3-(CF_2)_{1-2}-O-CF2-$, $CF_3-O-(CF_2)_{1-2}-O-CF_2-$, $CF_3-O-(CF_2-O)_{1-8}-$ and $CF_3-O-(CF_2-O)_{1-8}-CF_2-$.

In a variant, the perfluorinated group Rf may also preferably be selected from the groups $CF_3-(CF_2)_{0-3}-$, $CF_3-$ (CF$_2$)$_{0-3}$—O—, CF$_3$—O—(CF$_2$)$_{1-3}$— and CF$_3$—O—(CF$_2$)$_{1-3}$—O—, in particular from the groups CF$_3$—(CF$_2$)$_{1-2}$—, CF$_3$—(CF$_2$)$_{1-2}$—O—, CF$_3$—O—(CF$_2$)$_{1-2}$— and CF$_3$—O—(CF$_2$)$_{1-2}$—O—.

In particular, preference is given to compounds of the formulae (Ia) to (Ih) and/or (I'a) to (I'h) in which Rf is one of the preferred or particularly preferred groups and R''=C1- or C2-alkyl and/or R'''=H or methyl. Particular preference is given here to compounds of the formulae (Ic) to (Ih) and/or (I'a), (I'c) and (I'e), in particular with the preferred Rf, R'', R''' and R$^1$ groups.

An advantage of the novel compounds is that they are readily degradable. They have specific nominal breaking points in the molecule. Thus, corresponding low-molecular-weight fragments are able to form, which are able to enter the atmosphere and can thus be decomposed in the stratosphere under UV light.

Hydrofluoroethers of the following structure can be converted into readily volatile and UV-decomposable compounds, for example by hydrolysis and oxidation. The decomposition products can then be washed out of the atmosphere with the rain, transferred into the ground and mineralised there.

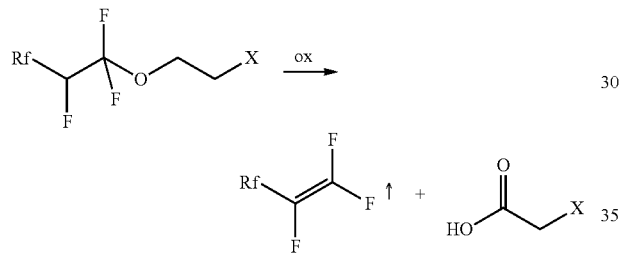

The group X here represents a reactive anchor group which is particularly suitable for adhering, for example, to glass surfaces (for example trialkoxysilanes).

The compounds of the formulae (I) and (I') can easily be synthesised. The starting materials used for the preparation of the compounds of the formula (I) are commercially available and/or their preparation starting from commercially available starting materials is familiar to the person skilled in the art or they can be prepared analogously to known synthetic processes, for example free-radical addition see: A. A. Il'in et al., Russian Journal of Applied Chemistry, 2007, Vol. 80, No. 3, pp. 405-418.

The preferred compounds of the formula (I) and (I') which belong to the substance class of the organosilanes can be achieved by the following simple synthesis, as shown by way of example for the methoxysilanes of the formula (I):

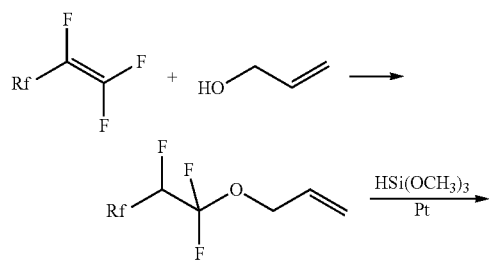

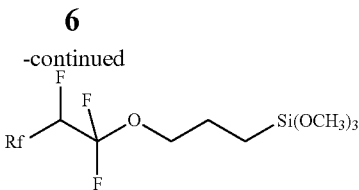

In order to obtain branched hydrofluoroether-silanes, the perfluoroolefins are reacted with bifunctional hydroxyalkenes.

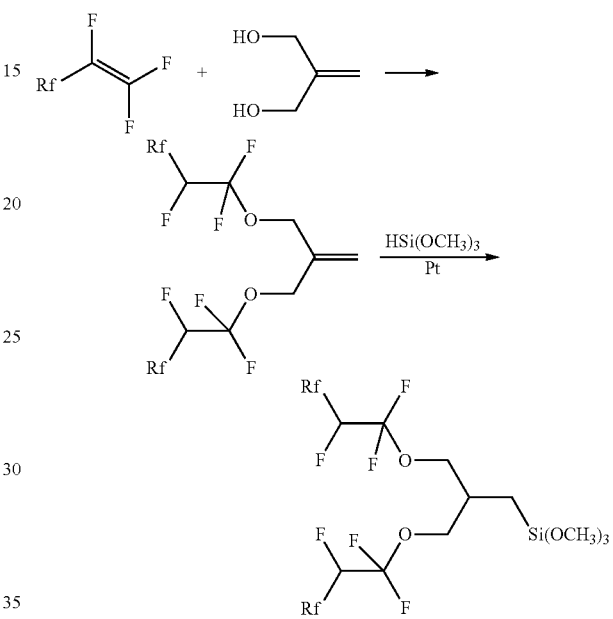

The trimethoxysilanes can then easily be dispersed in a suitable solvent and applied to the surface to be treated, for example glass. The trimethoxysilane hydrolyses by means of atmospheric moisture and forms a permanent covalent bond, for example, with the SiOH groups of the glass.

Compounds according to the invention containing acrylate or methacrylate groups can be prepared, for example, by reaction of the corresponding alcohols with the acids or acid anhydrides by methods known to the person skilled in the art.

The corresponding compounds of the formula (I') can be prepared via the reaction of the corresponding perfluoroolefins with the corresponding thio compounds. The reaction of perfluoropropyl vinyl ethers with 2-mercaptoethanol or 1,4-dimercaptobutane-2,3-diol and the further conversion into compounds of the formula (I'c) or (I'e) may be mentioned by way of example.

The invention also relates to a process for the preparation of compounds of the formula (I') according to one or more of claims 1 to 14 comprising a) the reaction of perfluoroalkyl vinyl ethers of the formula Rf—CF=CF$_2$ with mercaptoalcohols of the formula (HS)x-alkyl-(OH)y to give compounds of the formula (Rf—CHF—CF$_2$—S)$_x$-alkyl-(OH)$_y$, and b) the reaction of the compounds prepared in a) with unsaturated acids or acid anhydrides, where Rf=a perfluorinated alkyl group, optionally containing heteroatoms, and x and y, independently of one another, are ≥1.

The perfluorinated group Rf is preferably selected from the groups:

CF$_3$—(CF$_2$)$_{0-3}$—, CF$_3$—(CF$_2$)$_{0-3}$—O—, CF$_3$—(CF$_2$)$_{0-3}$—O—(CF$_2$)$_{1-3}$—, CF$_3$—(CF$_2$)$_{0-3}$—O—(CF$_2$)$_{1-3}$—O—, CF$_3$—(CF$_2$)$_{0-3}$—O—(CF$_2$)$_{1-3}$—O—CF$_2$—, CF$_3$—(CF$_2$)$_{0-3}$O—(CF$_2$—O)$_{1-8}$— and CF$_3$—(CF$_2$)$_{0-3}$—O—(CF$_2$—O)$_{1-8}$—CF$_2$—.

The perfluorinated group R$_f$ is particularly preferably selected from the groups:

CF$_3$—(CF$_2$)$_{1-2}$—, CF$_3$—(CF$_2$)$_{1-2}$—O—, CF$_3$—O—(CF$_2$)$_{1-2}$—, CF$_3$—O—(CF$_2$)$_{1-3}$—O—, CF$_3$—(CF$_2$)$_{1-2}$—O—CF$_2$—, CF$_3$—O—(CF$_2$)$_{1-2}$—O—CF$_2$—, CF$_3$—O—(CF$_2$—O)$_{1-8}$— and CF$_3$—O—(CF$_2$—O)$_{1-8}$—CF$_2$—, in particular CF$_3$—(CF$_2$)$_{1-2}$—, CF$_3$—(CF$_2$)$_{1-2}$—O— and CF$_3$—O—(CF$_2$)$_{1-3}$—O—.

Preferred sulfur-containing intermediates here are compounds of the formulae (II), (III) and (IV), where Rf=a perfluorinated alkyl group, optionally containing heteroatoms, as described above, and R$^1$ is equal to H or C1-C4-alkyl, preferably H or CH$_3$:

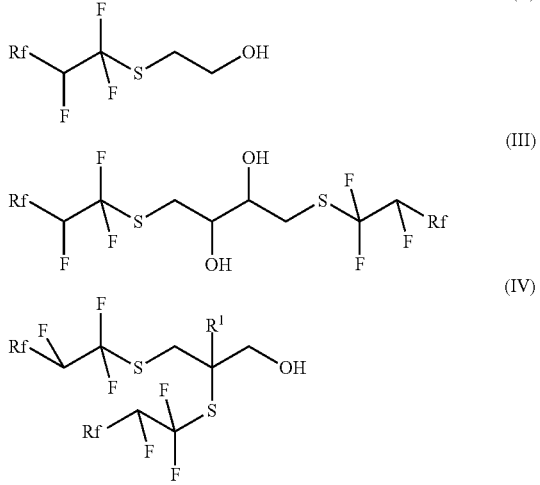

Preference is given to compounds of the formulae (II), (III) and (IV) in which the perfluorinated group Rf is selected from the groups:

CF$_3$—(CF$_2$)$_{0-3}$—, CF$_3$—(CF$_2$)$_{0-3}$—O—, CF$_3$—(CF$_2$)$_{0-3}$O—(CF$_2$)$_{1-3}$—, CF$_3$—(CF$_2$)$_{0-3}$—O—(CF$_2$)$_{1-3}$—O—, CF$_3$—(CF$_2$)$_{0-3}$—O—(CF$_2$)$_{1-3}$—O—CF$_2$—, CF$_3$—(CF$_2$)$_{0-3}$O—(CF$_2$—O)$_{1-8}$— and CF$_3$—(CF$_2$)$_{0-3}$—O—(CF$_2$—O)$_{1-8}$—CF$_2$—.

Particular preference is given to compounds of the formulae (II), (III) and (IV) in which the perfluorinated group Rf is selected from the groups:

CF$_3$—(CF$_2$)$_{1-2}$—, CF$_3$—(CF$_2$)$_{1-2}$—O—, CF$_3$—O—(CF$_2$)$_{1-3}$—, CF$_3$—O—(CF$_2$)$_{1-3}$—O—, CF$_3$—(CF$_2$)$_{1-2}$—O—CF2—, CF$_3$—O—(CF$_2$)$_{1-2}$—O—CF$_2$—, CF$_3$—O—(CF$_2$—O)$_{1-8}$— and CF$_3$—O—(CF$_2$—O)$_{1-8}$—CF$_2$—.

In a variant, the perfluorinated group Rf may also preferably be selected from the groups CF$_3$—(CF$_2$)$_{0-3}$—, CF$_3$—(CF$_2$)$_{0-3}$—O—, CF$_3$—O—(CF$_2$)$_{1-3}$— and CF$_3$—O—(CF$_2$)$_{1-3}$—O—, in particular from the groups CF$_3$—(CF$_2$)$_{1-2}$—, CF$_3$—(CF$_2$)$_{1-2}$—O—, CF$_3$—O—(CF$_2$)$_{1-2}$— and CF$_3$—O—(CF$_2$)$_{1-2}$—O—.

In particular, preference is given to compounds of the formulae (II), (III) and (IV) in which Rf is one of the preferred or particularly preferred groups and R$^1$ is equal to H or CH$_3$.

Particular preference is given to compounds of the formulae (IIa), (IIIa) and (IVa) where Rf'=CF$_3$—(CF$_2$)$_{1-2}$—, CF$_3$—O—(CF$_2$)$_{1-3}$—, CF$_3$—(CF$_2$)$_{1-2}$—O—CF$_2$—, CF$_3$—O—(CF$_2$)$_{1-2}$—O—CF$_2$— and CF$_3$—O—(CF$_2$—O)$_{1-8}$—CF$_2$— and R$^1$=H or CH$_3$:

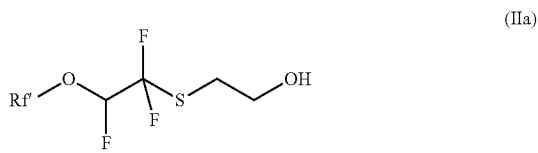

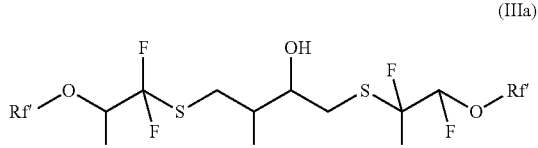

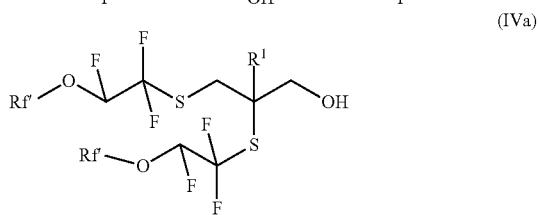

The syntheses shown in the examples can be used analogously for the preparation of further compounds of the formulae (I), (I'), (Ia)-(Ih) and (I'a)-(I'h), or also for the preparation of further intermediates of the formulae (II), (III) and (IV).

The compounds of the formulae (I) and (I'), preferably the compounds of the formulae (Ia) to (Ih) and (I'a) to (I'h), can preferably be degraded by a process for the degradation of fluorine-containing compounds comprising the following steps:

a) biological and/or abiotic degradation of the carbon skeleton of the fluorine-containing compounds with formation of, preferably non-toxic, fluorine-containing compounds, preferably having an adequately high vapour pressure, b) conversion of the fluorine-containing compounds formed in step a) into a gas phase, c) degradation of the fluorine-containing compounds formed in step a) into low-molecular-weight compounds by UV irradiation in the gas phase, d) conversion of the low-molecular-weight compounds formed in step c) from the gas phase into a liquid and/or solid phase, e) mineralisation of the low-molecular-weight compounds formed step c) in the liquid and/or solid phase.

Preferably, no fluorine-containing, salts are formed in step a). In particular, no perfluorinated compounds are formed in step a). The fluorine-containing compounds formed in step a) preferably have a sufficiently high vapour pressure in order to enable them to convert or be converted easily into the gas phase, preferably at atmospheric pressure.

The compounds according to the invention can be used alone or in the form of a mixture, also with other fluorinated and/or non-fluorinated compounds, in particular for the production of functional coatings and surface modifications of all types on articles both for inside and outside areas. In principle, all surfaces can be coated, in particular glass, ceramic, enamel, metals, plastics, elastomers, natural products, textiles, if necessary after suitable pretreatment.

The present invention furthermore relates to the use of the compounds of the formula (I) and/or (I') according to the invention, or of preferred compounds of the formulae (Ia) to (Ih) and/or (I'a) to (I'h), and the preferred embodiments described above, for the production of, for example, dirt-repellent and/or hydrophobic, coatings, in particular also for textile finishing and glass coating, for example of coatings in the display industry.

Besides the compounds of the formulae (I) and/or (I'), or the preferred compounds of the formulae (Ia) to (Ih) and/or (I'a) to (I'h), the coatings may also comprise solvents, additives, surfactants, assistants and fillers. Mention may also be made by way of example of silicone particles and, optionally surface-modified, pigments.

Preferred areas of use are, for example, the use of the compounds according to the invention in coatings for optical elements or textiles, such as, for example, the use in anti-fingerprint coatings, for example for displays, optical lenses, spectacle lenses, camera lenses, binoculars, window panes or mirrors, or as hydrophobicising agents for textile finishing.

The compounds according to the invention or mixtures comprising them can be applied to a suitable surface, over the entire area or a part-area, by various coating processes known to the person skilled in the art, for example by means of CVD, PVD, spray coating, ink-jet, offset processes.

The present invention relates to all uses mentioned here of compounds to be employed in accordance with the invention. The respective use of compounds of the formulae (I) and/or (I'), or of the preferred compounds of the formulae (Ia) to (Ih) and/or (I'a) to (I'h), for the said purposes is known to the person skilled in the art, and consequently the use of the compounds to be employed in accordance with the invention causes no problems.

The invention also relates to compositions which comprise at least one of the compounds according to the invention, where the compositions may also comprise solvents, additives, surfactants, assistants and fillers.

The invention also relates to coated articles, in particular the above-mentioned articles, whose coating has been produced using at least one compound according to the invention. Preference is given to displays, optical lenses, spectacle lenses, camera lenses, binoculars, window panes, mirrors and textiles.

The following examples explain the present invention in greater detail without restricting the scope of protection.

EXAMPLES

Abbreviations
TEMPO 2,2,6,6-tetramethylpiperidinyloxyl
THF tetrahydrofuran
MTBE tert-butyl methyl ether
RT room temperature Example 1

Synthesis of a compound of the Formula (Id) Where $R^1$=H, $R'''$=$CH_3$ and Rf=$C_3F_7$—O

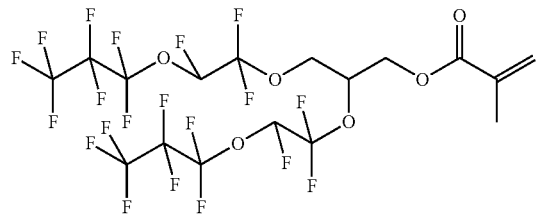 [SMILES: C=C(C)C(=O)OCC(COC(F)(F)C(F)OC(F)(F)C(F)(F)C(F)(F)F)OC(F)(F)C(F)OC(F)(F)C(F)(F)C(F)(F)F]

Example 1a:

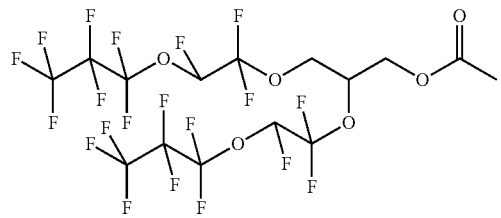 [SMILES: CC(=O)OCC(COC(F)(F)C(F)OC(F)(F)C(F)(F)C(F)(F)F)OC(F)(F)C(F)OC(F)(F)C(F)(F)C(F)(F)F]

100 g of 2,3-dihydroxypropyl acetate, 595 g of perfluoropropyl vinyl ether, 134 g of potassium carbonate and 460 g of acetonitrile are stirred at 80° C. in a pressure container for 70 hours. The internal pressure increases to 4 bar during the reaction. The reaction product is washed out of the reactor with 100 ml of acetonitrile, the mixture is filtered, and the solvent is separated off in a rotary evaporator, and the crude product is distilled under reduced pressure (b.p. 75° C. at 0.3 mbar). Yield: 533 g=80%. 1H-NMR: 6.8 ppm (m, 2 H, —CFH); 4.8 ppm (m, 1 H, —OCH); 4.3 ppm (m, 4H, —CH2); 2.1 ppm (s, 3 H, O=$CCH_3$)

Example 1b:

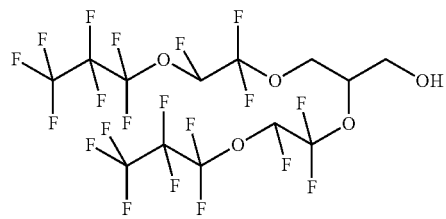 [SMILES: OCC(COC(F)(F)C(F)OC(F)(F)C(F)(F)C(F)(F)F)OC(F)(F)C(F)OC(F)(F)C(F)(F)C(F)(F)F]

30 g of ester are hydrogenated with 20 ml of methanol, 0.5 g of sodium methoxide, 27 mg of Ru-MACHO (Takasago International, JP) using hydrogen in a pressure reactor at 50 bar and 40° C. for 12 hours. 50 ml of methyl tert-butyl ether and 50 ml of water are added to the reaction mixture. The organic phase is separated off and dried over NaSO4. The product is freed from the solvent and distilled in vacuo (b.p.: 74° C. at 0.4 mbar). Yield: 20 g=70%).
1H-NMR: 6.8 ppm (m, 2 H, —CFH); 4.8-4.3 ppm (m, 5H, —CH2);

Example 1c:

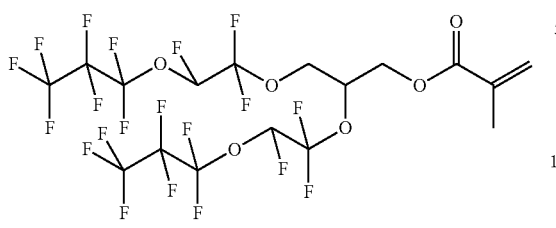

10 g of fluoroalcohol alcohol are dissolved in 35 ml of toluene with 0.5 g of toluene-4-sulfonic acid monohydrate. 2.7 g of methacrylic anhydride are then slowly added with stirring, and the reaction mixture is stirred at 110° C. for 24 h. 25 ml of water and 25 ml of MTBE are added to the batch, which has been cooled to room temperature, and separated off in a separating funnel. The aqueous phase is subsequently washed twice with 25 ml of MTBE. The combined organic phase is dried sodium sulfate and filtered. The solvent is subsequently distilled in a rotary evaporator. Yield: 9.98 g 1H-NMR: 6.8 ppm (m, 2 H, —CFH); 6.0 ppm (d, 1H, =CH); 5.6 ppm (d, 1H, =CH); 4.8-4.3 ppm (m, 5H, —CH2); 1.7 ppm (s, 3H, —CH3)

Example 2

Synthesis of a Compound of the Formula (I'e) Where R'''=CH₃ and Rf=C₃F₇—O

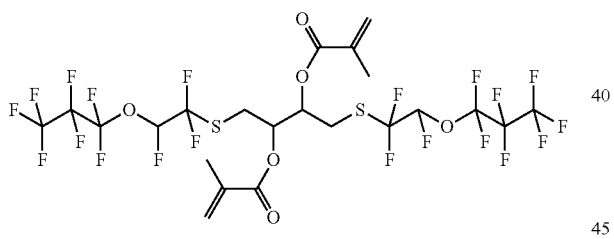

Example 2a:

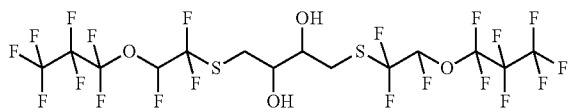 [SMILES: OC(CSC(F)(F)C(F)OC(F)(F)C(F)(F)C(F)(F)F)C(O)CSC(F)(F)C(F)OC(F)(F)C(F)(F)C(F)(F)F]

8.63 g of perfluoropropyl vinyl ether are heated at 120° C. in a pressure reactor for 18 hours with 2.5 g of 1,4-dimercaptobutane-2,3-diol, 25 ml of acetonitrile and 0.67 g of potassium carbonate. 25 ml of water and 25 ml of MTBE are added to the reaction mixture, and the phases are separated. The aqueous phase is extracted with 2×25 ml of MTBE, and the combined organic phase washed with 70 ml of water and 70 ml of saturated NaCl solution. The extract is dried over sodium sulfate, and the solvent is distilled.

Yield: 9.82 g=88%

1H-NMR: 6.8 ppm (d, 2 H, —CFH); 3.6 ppm (m, 2H, —CHOH); 3.0 ppm (m, 4H, —SCH2);

Example 2b:

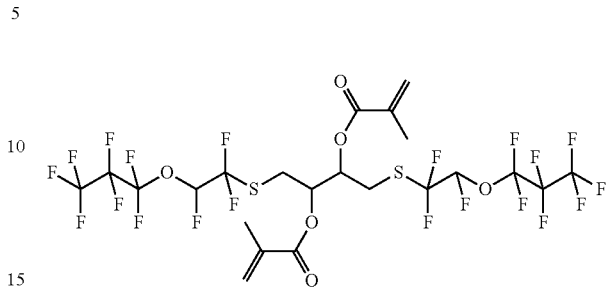

10 g of fluoroalcohol alcohol are dissolved in 35 ml of toluene with 0.5 g of toluene-4-sulfonic acid monohydrate. 4.5 g of methacrylic anhydride are then slowly added with stirring, and the reaction mixture is stirred at 110° C. for 24 h. 25 ml of water and 25 ml of MTBE are added to the batch, which has been cooled to room temperature, and separated off in a separating funnel. The aqueous phase is subsequently washed twice with 25 ml of MTBE. The combined organic phase is dried sodium sulfate and filtered. The solvent is subsequently removed in a rotary evaporator. Yield: 14.5 g 1 H-NMR: 6.8 ppm (m, 2 H, —CFH); 6.0 ppm (d, 2H, =CH); 5.6 ppm (d, 2H, =CH); 3.6 ppm (m, 2H, —OCH—); 3.0 ppm (m, 4H, —SCH2); 1.6 ppm (s, 6H, —CH3)

Example 3

Synthesis of a Compound of the Formula (I'c) where R'''=CH₃ and Rf=C₃F₇—O

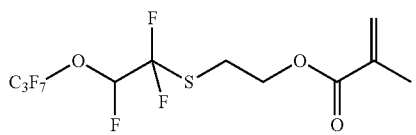

Example 3a:

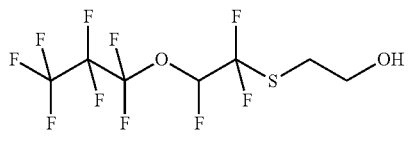 [SMILES: OCCSC(F)(F)C(F)OC(F)(F)C(F)(F)C(F)(F)F]

77.30 g of perfluoropropyl vinyl ether are heated at 100° C. in a pressure reactor for 18 hours with 52.21 g of 2-mercaptoethanol 40 ml of acetonitrile and 12 g of potassium carbonate. 25 ml of water and 25 ml of MTBE are added to the reaction mixture, and the phases are separated. The aqueous phase is extracted with 2×25 ml of MTBE, and the combined organic phase washed with 70 ml of water and 70 ml of saturated NaCl solution. The extract is dried over sodium sulfate, the solvent is removed, and the crude material is distilled (b.p. 45-49° C. at 0.1 mbar). Yield: 63.40 g=63%

1H-NMR: 6.8 ppm (dt, 1 H, —CFH); 3.6 ppm (t, 2H, —CH2O—); 3.1 ppm (t, 2H, —SCH2);

Example 3b:

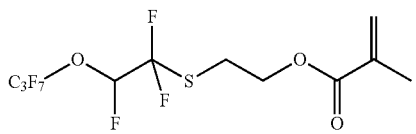

10 g of fluoroalcohol alcohol are dissolved in 60 ml of toluene with 0.5 g of toluene-4-sulfonic acid monohydrate. 4.5 g of methacrylic anhydride are then slowly added with stirring, and the reaction mixture is stirred at 110° C. for 24 h. 25 ml of water and 25 ml of MTBE are added to the batch, which has been cooled to room temperature, and separated off in a separating funnel. The aqueous phase is subsequently washed twice with 25 ml of MTBE. The combined organic phase is dried sodium sulfate, filtered, and the solvent is removed in a rotary evaporator.

Yield: 11.30 g=94%

1H-NMR: 7.1 ppm (m, 1 H, —CFH); 6.1 ppm (m, 1H, =CH); 5.7 ppm (m, 1H, =CH); 4.3 ppm (t, 2H, —CH2O—); 3.2 ppm (t, 2H, —SCH2); 1.9 ppm (s, 3H, —CH3)

Example 4

Synthesis of a Compound of the Formula (Id) where R'''=CH$_3$, R$^1$=CH$_3$ and Rf=CF$_3$—O—C$_3$F$_6$—O

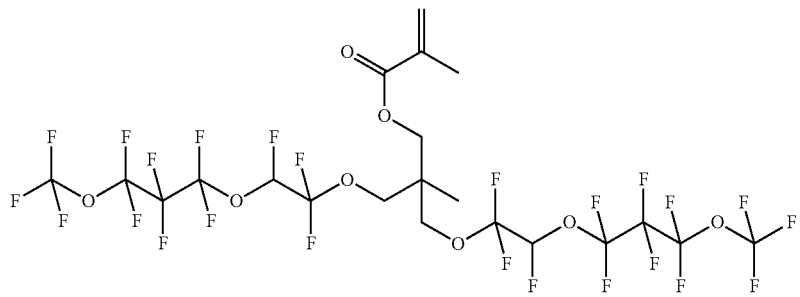 [SMILES: C=C(C)C(=O)OCC(C)(COC(F)(F)C(F)OC(F)(F)C(F)(F)C(F)(F)OC(F)(F)F)COC(F)(F)C(F)OC(F)(F)C(F)(F)C(F)(F)OC(F)(F)F]

Example 4a:

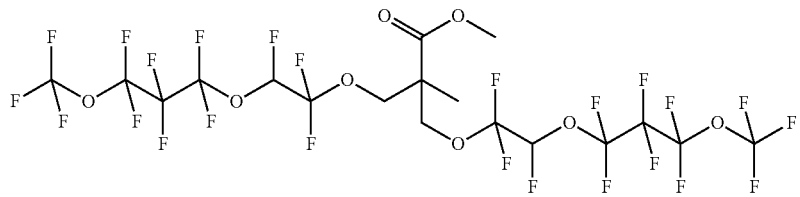 [SMILES: COC(=O)C(C)(COC(F)(F)C(F)OC(F)(F)C(F)(F)C(F)(F)OC(F)(F)F)COC(F)(F)C(F)OC(F)(F)C(F)(F)C(F)(F)OC(F)(F)F]

5 g of methyl 3-hydroxy-2-hydroxymethyl-2-methylpropionate, 20 ml of 1,1,2,2,3,3-hexafluoro-1-trifluoromethoxy-3-trifluorovinyloxypropane 60 ml of acetonitrile and 6 g of potassium carbonate are stirred at 80° C. in a pressure reactor for 20 h. A pressure of 1.5 bar became established. The reaction is terminated, and water and MTBE are added to the reaction mixture. The phases are separated, and the aqueous phase is extracted with 2×50 ml of MTBE. The combined organic phase is subsequently washed with 70 ml of water and 70 ml of NaCl solution. The extract is dried over sodium sulfate, and the solvent is distilled.

Product weight: 20.58 g 75%

1H-NMR: 6.6 ppm (m, 2 H, —CFH); 4.2 ppm (dd, 4H, —CH2O); 3.7 ppm (s, 3H, —OCH3); 1.25 ppm (s, 3H CCH3)

Example 4b:

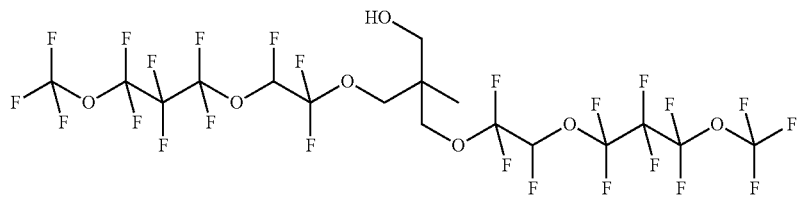 [SMILES: CC(CO)(COC(F)(F)C(F)OC(F)(F)C(F)(F)C(F)(F)OC(F)(F)F)COC(F)(F)C(F)OC(F)(F)C(F)(F)C(F)(F)OC(F)(F)F]

20 g of ester are hydrogenated with 15 ml of methanol, 0.3 g of sodium methoxide, 15 mg of catalyst using hydrogen in a pressure reactor at 50 bar and 40° C. for 12 hours. 50 ml of methyl tert-butyl ether and 50 ml of water are added to the reaction mixture, the organic phase is separated off and dried over NaSO4. The product is freed from the solvent and distilled in vacuo (b.p.: 95° C. at 0.1 mbar).

Yield: 16 g=82%).

1H-NMR: 6.6 ppm (m, 2 H, —CFH); 6.1 ppm (m, 1H, =CH); 5.7 ppm (m, 1H, =CH); 4.3-4.1 ppm (m, 6H, —CH2O); 1.3 ppm (s, 3H CCH3)

Example 4c:

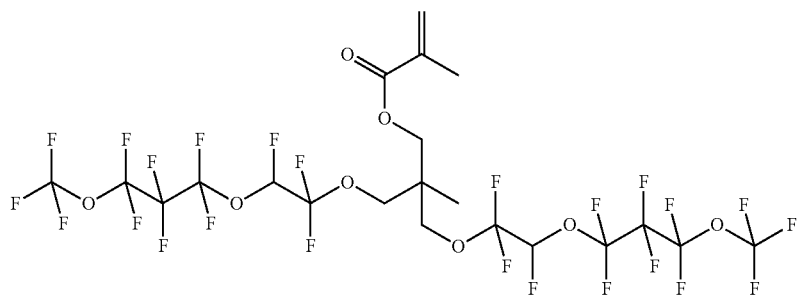 [SMILES: C=C(C)C(=O)OCC(C)(COC(F)(F)C(F)OC(F)(F)C(F)(F)C(F)(F)OC(F)(F)F)COC(F)(F)C(F)OC(F)(F)C(F)(F)C(F)(F)OC(F)(F)F]

10 g of fluoroalcohol alcohol are dissolved in 35 ml of toluene with 0.5 g of toluene-4-sulfonic acid monohydrate. 2 g of methacrylic anhydride are then slowly added with stirring, and the reaction mixture is stirred at 110° C. for 24 h. 25 ml of water and 25 ml of MTBE are added to the batch, which has been cooled to room temperature, and separated off in a separating funnel. The aqueous phase is subsequently washed twice with 25 ml of MTBE, and the combined organic phase is dried using sodium sulfate and filtered. The solvent is removed in a rotary evaporator. Yield: 10.5 g=96%

1H-NMR: 6.6 ppm (m, 2 H, —CFH); 6.2 ppm (m, 1H, =CH); 5.7 ppm (m, 1H, =CH); 4.3-4.1 ppm (m, 6H, —CH2O); 1.9 ppm (s, 3H, —CH3); 1.25 ppm (s, 3H CCH3)

Example 5

Synthesis of a Compound of the Formula (Ih) Where R'''=CH$_3$ and Rf=C$_3$F$_7$—O

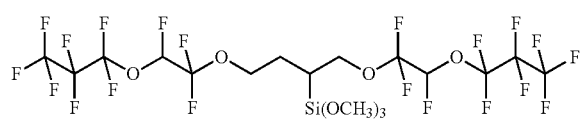

Example 5a:

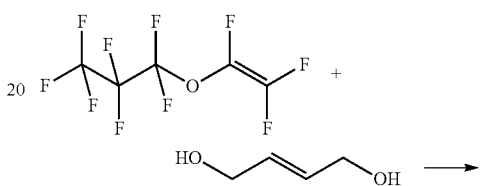

-continued

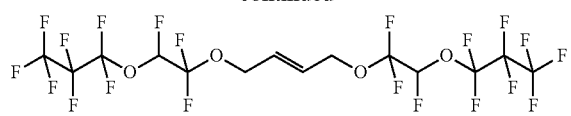

3.56 g of but-2-en1,4-diol and 26.87 g of perfluorovinyloxypropane are heated to 80° C. in an autoclave with 2.84 g of KOH and 27.5 g of acetonitrile and brought to reaction at this temperature for 24 h. During this time, the internal pressure drops from initially 2.6 bar to 1 bar. After cooling to room temperature, the batch is filtered and the solvent is distilled. The solvent is removed in vacuo. Crude yield yield: m=30.28 g The crude product is dissolved in 30 ml of acetonitrile, 20 ml of toluene are added, causing a white gel to precipitate out. The precipitate is filtered off via a little silica gel and rinsed with 20 ml of acetonitrile. After removal of the solvent, the residue is dried.

Yield: m=24.8 g

1H-NMR: 6.7 ppm (m, 2 H, —CFH); 6.0 ppm (s, 2H, =CH); 4.6 ppm (s, 4H, —CH2O);

Example 5b:

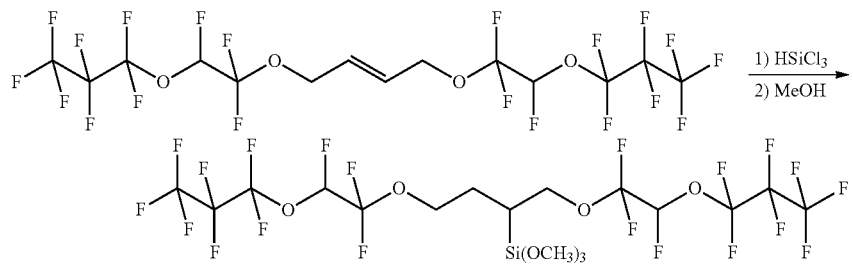

0.15 g of hexachloroplatinic(IV) acid hexahydrate (~40% of Pt) and 10 g of perfluoroolefin in 12 ml of abs. THF are initially introduced in a 100 ml four-necked flask with ice-cooling and under argon. 1.84 ml of trichlorosilane are added to the batch via a syringe with stirring and ice-cooling at such a rate that the IT does not exceed 5° C. The batch is heated to 60° C. and brought to reaction at this temperature for 4 h. The mixture is subsequently cooled to RT under argon overnight. 5 ml of trimethyl orthoformate are added, and 2 ml of MeOH are subsequently added. During this addition, the temperature rises by 5K to 33° C. The mixture is warmed to 50° C. and stirred at this temperature for 2 h. The batch is cooled, the solvent is removed, and the residue is dried in vacuo. Crude yield: m=18.95 g The batch is purified at 120° C. in a bulb-tube distillation apparatus in a high vacuum.

1H-NMR: 6.7 ppm (dt, 2 H, —CFH); 3.8 ppm (m, 4 H, —OCH2); 3.5 ppm (s, 9H, —OCH3); 1.4 ppm (m, 2 H, —CH2); 0.6 ppm (m, 1 H, —SiCH);

Example 6

Synthesis of a Compound of the Formula (Ig) where R'''=CH₃ and Rf=C₃F₇—O

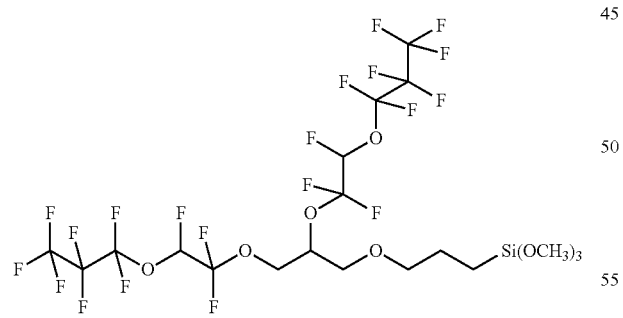

Example 6a:

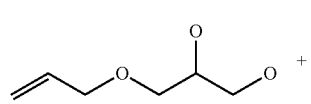

-continued

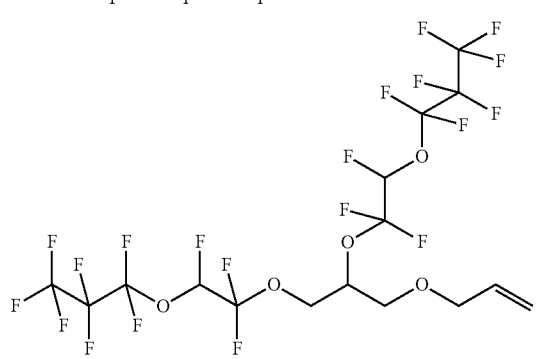

10.0 g of allyloxy-1,2-propanediol are brought to reaction with 60.4 g of perfluorovinyloxypropane, 13.6 g of potassium carbonate and 46.5 g of acetonitrile at 80° C. in an autoclave for 48 h. After completion, the batch is filtered, and the solvent is removed in vacuo. Yield: m=50.2 g The product is distilled in vacuo (64-65° C. at 3 mbar)

1H-NMR: 6.8 ppm (d, 2 H, —CFH); 5.9 ppm (m, 1H, CH); 5.3 ppm (d, 1H, =CH₂), 5.2 ppm (d, 1H, =CH₂), 4.8 ppm (d, 1H, =CH) 4.2 ppm (m, 2 H, —OCH₂); 4.0 ppm (m, 2 H, —OCH₂); 3.8 ppm (m, 2 H, —OCH₂)

Example 6b:

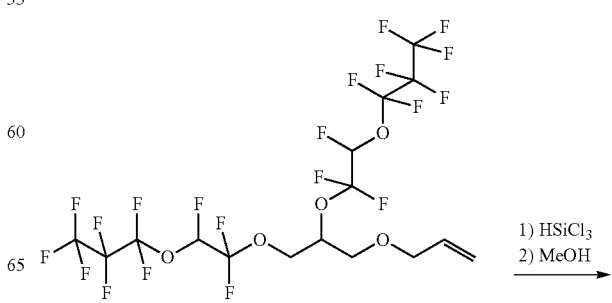

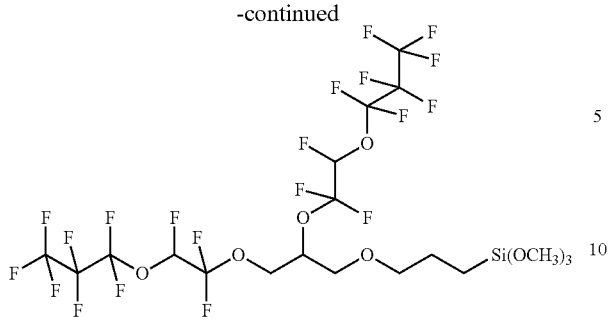

0.15 g of hexachloroplatinic (IV) acid hexahydrate (~40% of Pt) and 10 g of perfluoroolefin in 12 ml of abs. THF are initially introduced in a 100 ml four-necked flask with ice-cooling and under argon. 1.84 ml of trichlorosilane are added to the batch via a syringe with stirring and ice-cooling at such a rate that the IT does not exceed 5° C. The batch is heated to 60° C. and brought to reaction at this temperature for 4 h. The mixture is subsequently cooled to RT under argon overnight. 5 ml of trimethyl orthoformate are added, and 2 ml of MeOH are subsequently added. The batch is warmed to 50° C. and stirred at this temperature for 6 h. The batch is cooled, the solvent is removed, and the residue is dried in vacuo. Crude yield: m=15.2 g The product is purified in a bulb-tube distillation apparatus. 115° @ C 0.01 mbar 1H-NMR: 6.8 ppm (d, 2 H, —CFH); 5.9 ppm (m, 1H, CH); 4.2 ppm (m, 2H, —OCH$_2$); 4.0 ppm (m, 2H, —OCH$_2$); 3.5 ppm (s, 9H, —OCH$_3$); 3.4 ppm (m, 2H, —OCH$_2$) 1.5-0.6 ppm (m, 4H, CH$_2$—CH$_2$—Si—)

The invention claimed is:

1. A compound of formulae Ib, Id, Ie, Ig or Ih:

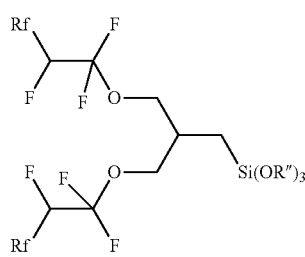
(Ib)

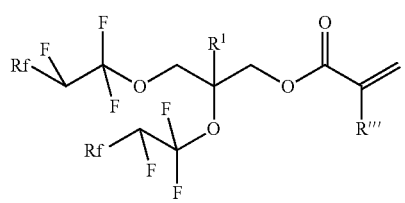
(Id)

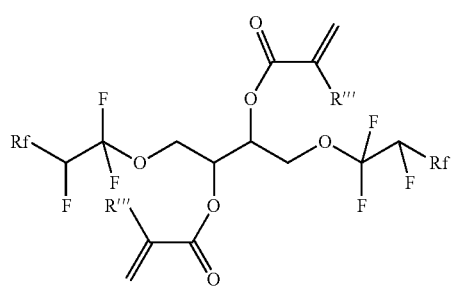
(Ie)

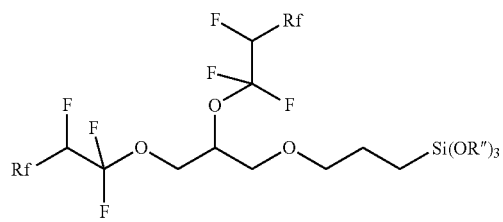
(Ig)

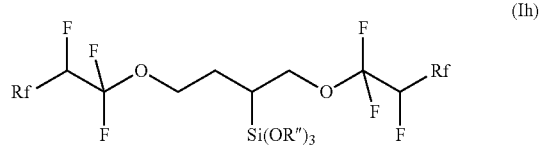
(Ih)

where

Rf=a perfluorinated alkyl group, optionally containing heteroatoms,

R$^1$=H or C$_1$-C$_4$-alkyl,

R''=C$_1$-C$_4$-alkyl, and R''''=H or an alkyl group.

2. The compound according to claim 1, wherein Rf is selected from CF$_3$—(CF$_2$)$_{0-3}$—O—, CF$_3$—(CF$_2$)$_{0-3}$—O—, CF$_3$—(CF$_2$)$_{0-3}$—O—(CF$_2$)$_{1-3}$—, CF$_3$—(CF$_2$)$_{0-3}$—O—(CF$_2$)$_{1-3}$—O—, CF$_3$—(CF$_2$)$_{0-3}$—O—(CF$_2$)$_{1-3}$—O—CF$_2$—, CF$_3$—(CF$_2$)$_{0-3}$—O—(CF$_2$—O—)$_{1-8}$— and CF$_3$—(CF$_2$)$_{0-3}$—O—(CF$_2$—O)$_{1-8}$—CF$_2$—.

3. The compound according to claim 1, wherein R$_f$ is selected from CF$_3$—(CF$_2$)$_{1-2}$—, CF$_3$—(CF$_2$)$_{1-2}$—O—, CF$_3$—O—(CF$_2$)$_{1-3}$—, CF$_3$—O—(CF$_2$)$_{1-2}$—O—, CF$_3$—(CF$_2$)$_{1-2}$—O—CF$_2$—, CF$_3$—O—(CF$_2$)$_{1-2}$—O—CF$_2$—, CF$_3$—O—(CF$_2$—O—)$_{1-8}$— and CF$_3$—O—(CF$_2$—O—)$_{1-8}$—CF$_2$—.

4. The compound according to claim 1, wherein R'' is C$_1$- or C$_2$-alkyl.

5. The compound according to claim 1, wherein the compound is of formula (Ib)

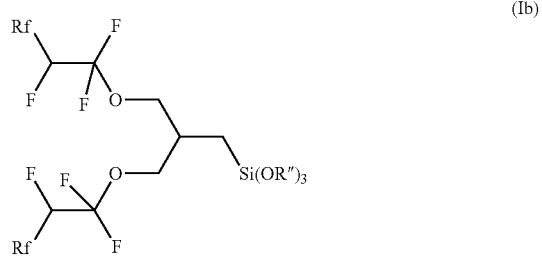
(Ib)

6. The compound according to claim 1, wherein Rf is CF$_3$—(CF$_2$)$_{1-2}$—, CF$_3$—(CF$_2$)$_{1-2}$—O—, CF$^3$—O—(CF$_2$)$_{1-3}$— or CF$_3$—O—(CF$_2$)$_{1-2}$—O—.

7. The compound according to claim 1, wherein the compound is of formula (Id)

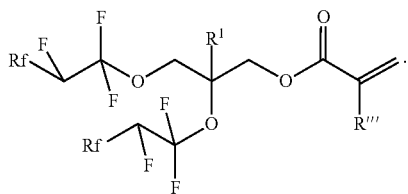
(Id)
8. The compound according to claim 1, wherein the compound is of formula (Ie)
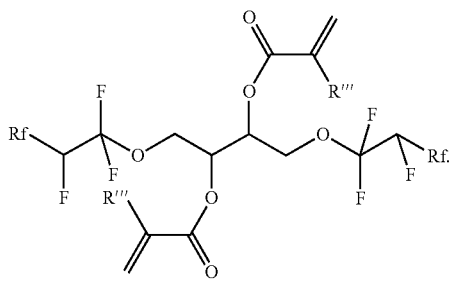
(Ie)
9. The compound according to claim 1, wherein the compound is of formula (Ig)
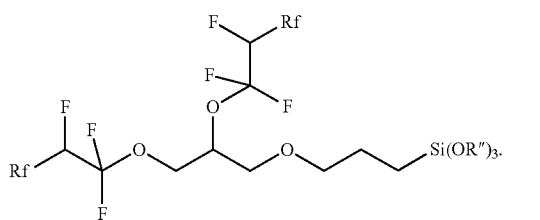
(Ig)
10. The compound according to claim 1, wherein the compound is of formula (Ih)
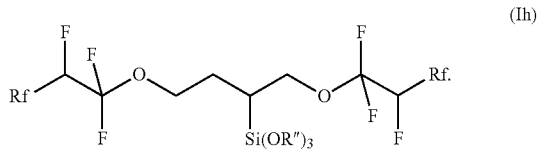
(Ih)
11. The compound according to claim 1, wherein the compound is selected from the following compounds:
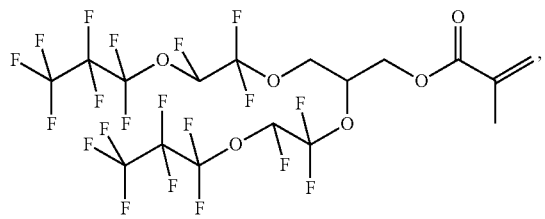
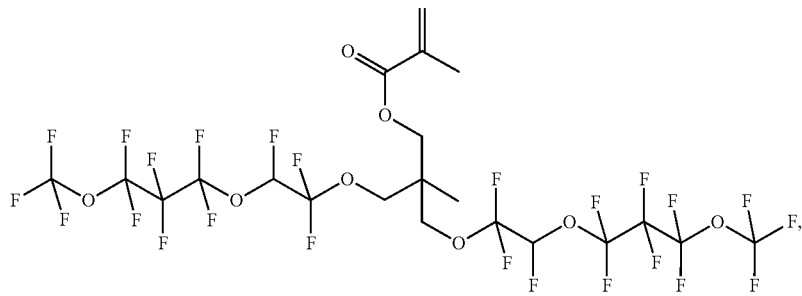
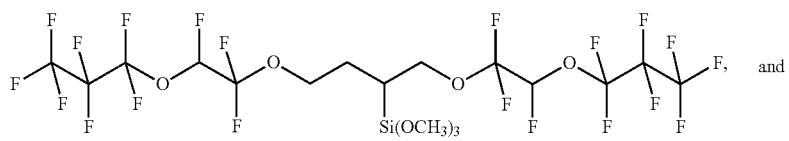

-continued

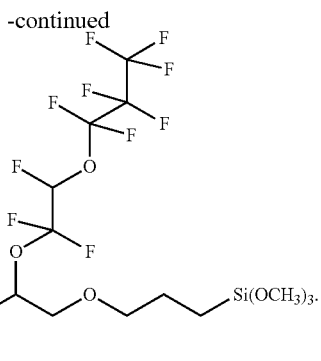

12. A method of providing a dirt-repellent surface to a substrate comprising applying to said substrate at least one compound according to claim 1.

13. A composition comprising at least one compound according to claim 1 and a support which is suitable for the respective application and optionally further additives.

14. A coated article having a coating produced using at least one compound according to claim 1.

* * * * *